(12) United States Patent
Shurtliff et al.

(10) Patent No.: US 6,187,209 B1
(45) Date of Patent: Feb. 13, 2001

(54) LINED SAMPLING VESSEL INCLUDING A FILTER TO SEPARATE SOLIDS FROM LIQUIDS ON EXIT

(75) Inventors: Rodney M. Shurtliff; Kerry M. Klingler, both of Idaho Falls; Terry D. Turner, Ammon, all of ID (US)

(73) Assignee: Bechtel BWXT Idaho, LLC, Idaho Falls, ID (US)

( * ) Notice: Under 35 U.S.C. 154(b), the term of this patent shall be extended for 0 days.

(21) Appl. No.: 09/533,462

(22) Filed: Mar. 23, 2000

(51) Int. Cl.⁷ .......................... B01D 37/00; B01D 35/027
(52) U.S. Cl. .................. 210/808; 210/406; 210/416.1; 210/464; 422/101; 422/102
(58) Field of Search .................. 210/808, 359, 210/406, 416.1, 446, 464; 422/101, 102

(56) References Cited

U.S. PATENT DOCUMENTS 4,990,253 * 2/1991 Vcelka .................. 210/359

* cited by examiner

Primary Examiner—Robert J. Popovics
(74) Attorney, Agent, or Firm—Klaas Law O'Meara & Malkin

(57) ABSTRACT

A filtering apparatus has an open canister with an inlet port. A canister lid is provided which includes an outlet port for the passage of fluids from the canister. Liners are also provided which are shaped to fit the interiors of the canister and the lid, with at least the canister liner preferably being flexible. The sample to be filtered is positioned inside the canister liner, with the lid and lid liner being put in place thereafter. A filter element is located between the sample and the outlet port. Seals are formed between the canister liner and lid liner, and around the outlet port to prevent fluid leakage. A pressure differential is created between the canister and the canister liner so that the fluid in the sample is ejected from the outlet port and the canister liner collapses around the retained solids.

19 Claims, 6 Drawing Sheets

LINED SAMPLING VESSEL INCLUDING A FILTER TO SEPARATE SOLIDS FROM LIQUIDS ON EXIT

CONTRACTUAL ORIGIN OF THE INVENTION

This invention was made with United States Government support under Contract No. DE-AC07-94ID13223, now Contract No. DE-AC07-99ID13727 awarded by the United States Department of Energy. The United States Government has certain rights in the invention.

FIELD OF THE INVENTION

This invention relates to a filter system that is easily and quickly cleaned and is adapted for handling potentially hazardous substances. More particularly, the invention relates to a filter system that is capable of handling substantially all solid-solvate combinations, particularly soil samples from sites being examined for potential toxicity. The invention features specially adapted liners that prevent contact between the samples to be filtered and the apparatus. The system is easy to assemble and disassemble.

BACKGROUND OF THE INVENTION

In the environmental clean-up of government facilities, one important aspect is the sampling of potentially contaminated soil. A considerable amount of work has been done taking soil samples, dissolving them in various organic and aqueous solvents, and analyzing the solvates. The solvates may contain constituents as diverse as viscous hydrocarbons, toxic chemicals, or nuclear waste. The soil samples themselves may consist of fine sands, chunks of various solids, some very abrasive or sharp, and liquids of unknown character.

When confronted with the need to rapidly prepare, filter and analyze many such environmental soil samples, various commercial devices were investigated. A representative, commercially available filter system of standard design is shown schematically in FIG. 1.

Referring to FIG. 1, canister 2 contains solids 4 from liquid 6 to be filtered. O-ring 8 forms a slideable sealing arrangement between inner walls 10 of canister 2 and pneumatic piston 12. Filter element 14 is located adjacent canister lid 16. O-rings 18 and 20 form a seal between lid 16 and filter element ring 22 which secures the filter element 14 in position.

To separate solids 4 from liquid 6, pressurized air 24 is delivered through inlet port 26. The air moves piston 12 and forces liquid 6 and any gases through outlet 28 in lid 16.

While the above-described apparatus is fairly effective at separating solids 4 from liquid 6, it is very difficult and time consuming to clean. Leakage around O-ring 8 was common, resulting in liquids contaminating the area around inlet port 26. Furthermore, piston 12 tended to get stuck in canister 2 and often had to be pounded out for cleaning. Difficulty disassembling the unit also tended to damage O-rings and seals, requiring at least partial replacement every cycle or risking potential leaks. These problems led to long turn-around times between processing samples. They also made the risk of cross-contamination of samples much greater.

Accordingly, there has been a long felt need for a fast, efficient, sanitary and easily cleaned filtering apparatus.

SUMMARY OF THE INVENTION

In accordance with a preferred embodiment of the invention, the claimed filtering apparatus comprises an open canister having an inlet port therein. A canister liner is provided for the open canister, with a solid-liquid sample being placed in the liner prior to filtering. The filtering apparatus further includes a canister lid that has an outlet port for filtered liquids. A liner is also provided for the canister lid. The canister and lid liners are shaped to fit the interiors of the canister and the lid, respectively, and the canister liner is flexible under filtering conditions. The sample to be filtered is placed in the canister liner prior to placing the canister lid on the open canister.

When the apparatus is assembled for filtering, a filter, preferably in a filter element assembly, is located adjacent the canister lid liner. When the lid is placed on the canister and clamped or otherwise held in place, the lid liner and the canister liner form a sealable relation with one another (that is, a seal is formed so that both components are sealably engaged together) to prevent liquid leakage outwardly from the assembled liner configuration discussed above. A hole or opening is provided in the canister lid liner to allow the exit of solvate liquid from the canister through the filter and out of the outlet port in the canister lid. The filter, lid liner and lid are also sealably engaged at the outlet port to prevent any liquid leakage.

A sample is filtered in a preferred embodiment by creating a pressure differential between the interior of the canister and the canister liner containing the sample. This process collapses the canister liner around the sample solids and forces the sample liquid through the outlet port. This may be accomplished by inverting the filtering apparatus and opening the inlet port to atmosphere.

The canister and lid liners are formed of a material that is chemically impervious to the sample and is tough enough to withstand abrasion from sample solids without puncturing or tearing. The canister liner must also be flexible under filtering conditions. A representative and non-limiting set of canister and lid liners may be compression molded from polytetrafluoroethylene sheet material. Use of the liners and seals as described herein prevents the interior surfaces of the canister and lid from being contaminated by the sample.

The subject filtering system is easily disassembled by removing the lid from the canister and then removing the liners and filter element. The system elements downstream of the outlet for solvate removal are flushed. New canister and lid liners and a clean filter are provided, readying the apparatus to filter another sample.

The invention will be better understood in terms of the several drawings and detailed description which follow.

DETAILED DESCRIPTION OF THE INVENTION

Figure 1:
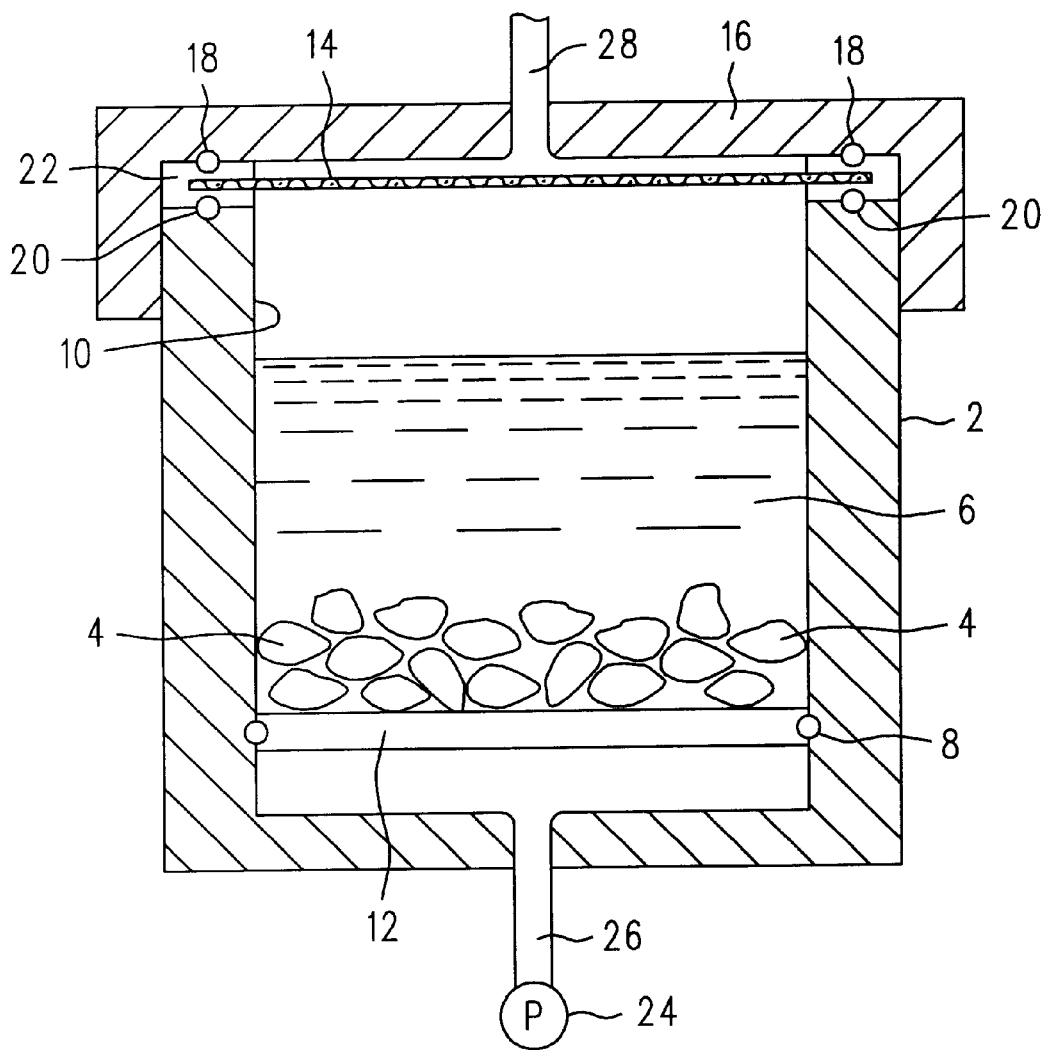
FIG. 1, discussed above, is a schematic cross-sectional view of a prior art apparatus.
Figure 2:
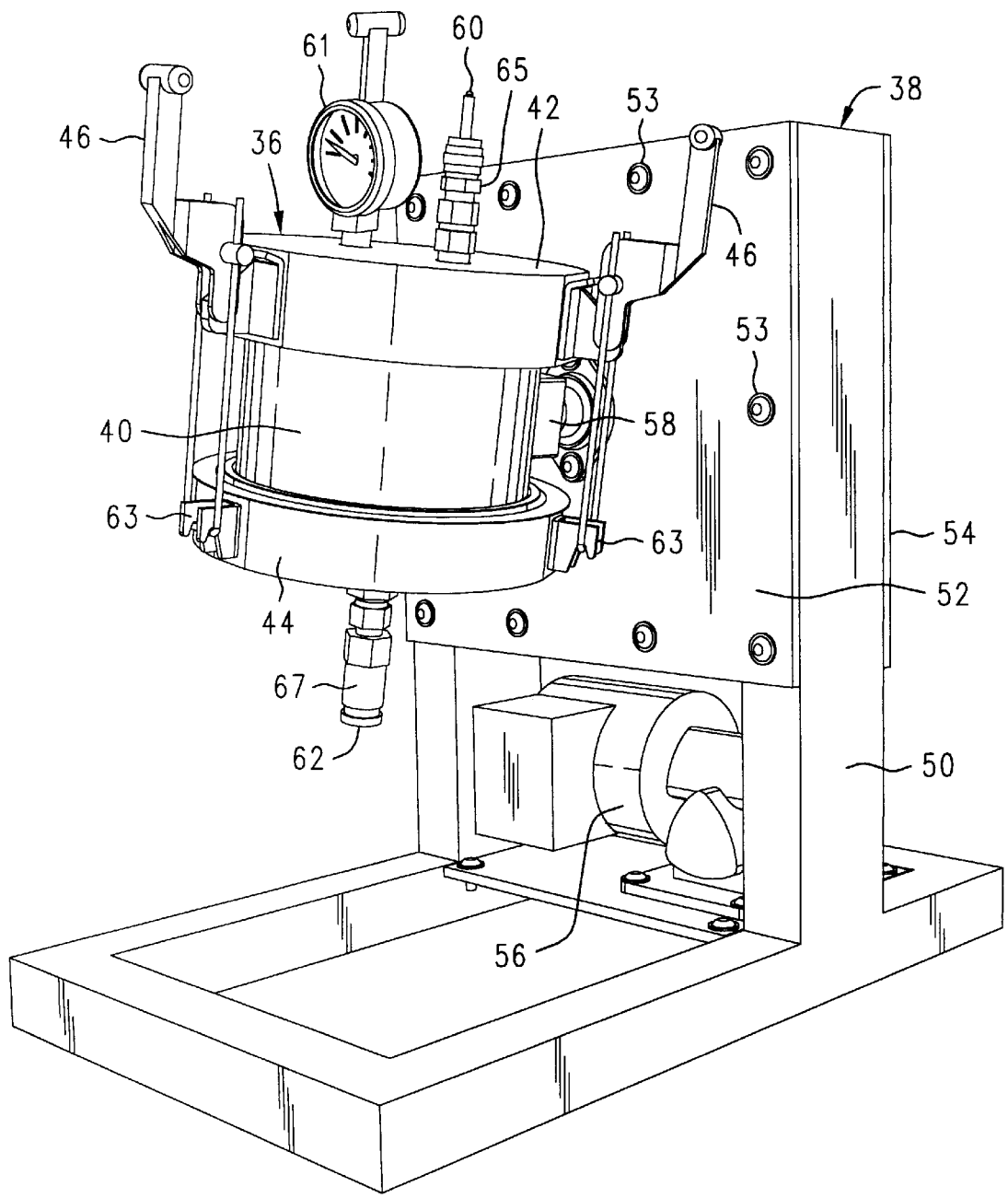
FIG. 2 is perspective, schematic view of an apparatus produced in accordance with the invention which is mounted on a device for rotating it.

In accordance with a preferred embodiment and with reference to FIG. 2, a schematic, perspective view of a filter system produced in accordance with the invention is shown. Filtering apparatus 36 is shown mounted on rotating device 38. Filtering apparatus 36 comprises open-ended canister body 40, lid 42 (also characterized herein as an "inlet lid") and lid 44 (also designated herein as an "outlet lid"). These elements may be machined from a metal such as aluminum or formed from an engineering plastic.

Outlet lid 44 and inlet lid 42 are preferably secured to canister body 40 by means of three toggle clamps 46 (one clamp hidden from view in FIG. 2) which are secured to catches 63. While the subject embodiment shows a detachable inlet lid 42, a canister with an integral lid would also be suitable for use in the invention.

Inlet port 60 is provided in inlet lid 42 and outlet port 62 is provided in outlet lid 44. Ports 60 and 62 may comprise a quick disconnect coupling 65 and 67, respectively, of a type well known to those skilled in the art. Rotating device 38 for apparatus 36 comprises frame 50, front plate 52 and back plate 54. Front plate 52 is attached to frame 50 by bolts 53. Motor 56 drives a chain (not shown) which causes mounting post 58 to rotate in a clockwise or counterclockwise direction, as desired, to agitate the contents of the filtering apparatus 36. Details of apparatus 36 will be better understood in terms of FIG. 3 which is an exploded perspective view of the filtering apparatus 36 of FIG. 2.

Figure 3:
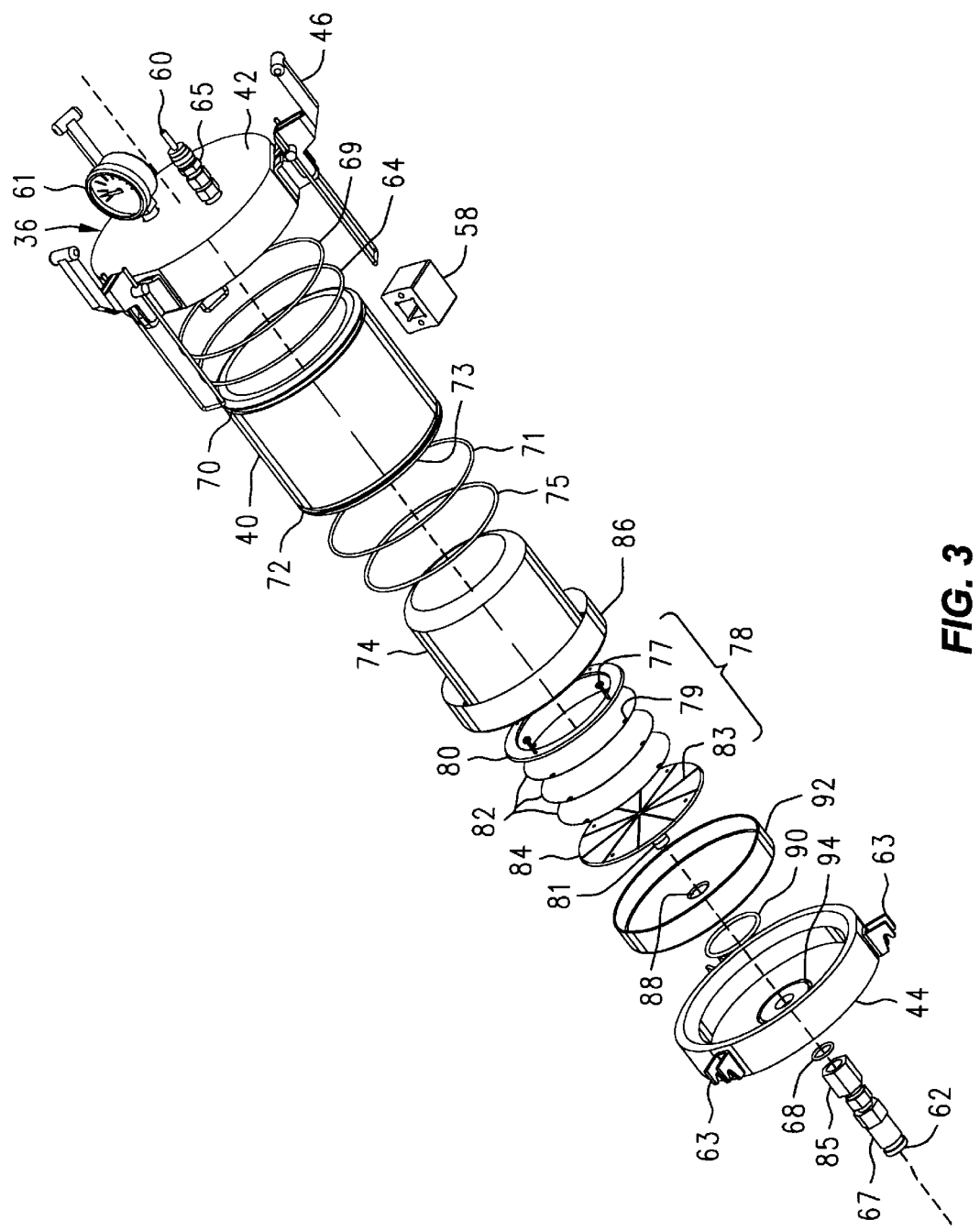
FIG. 3 is an exploded perspective view of the apparatus of FIG. 2.
Figure 6:
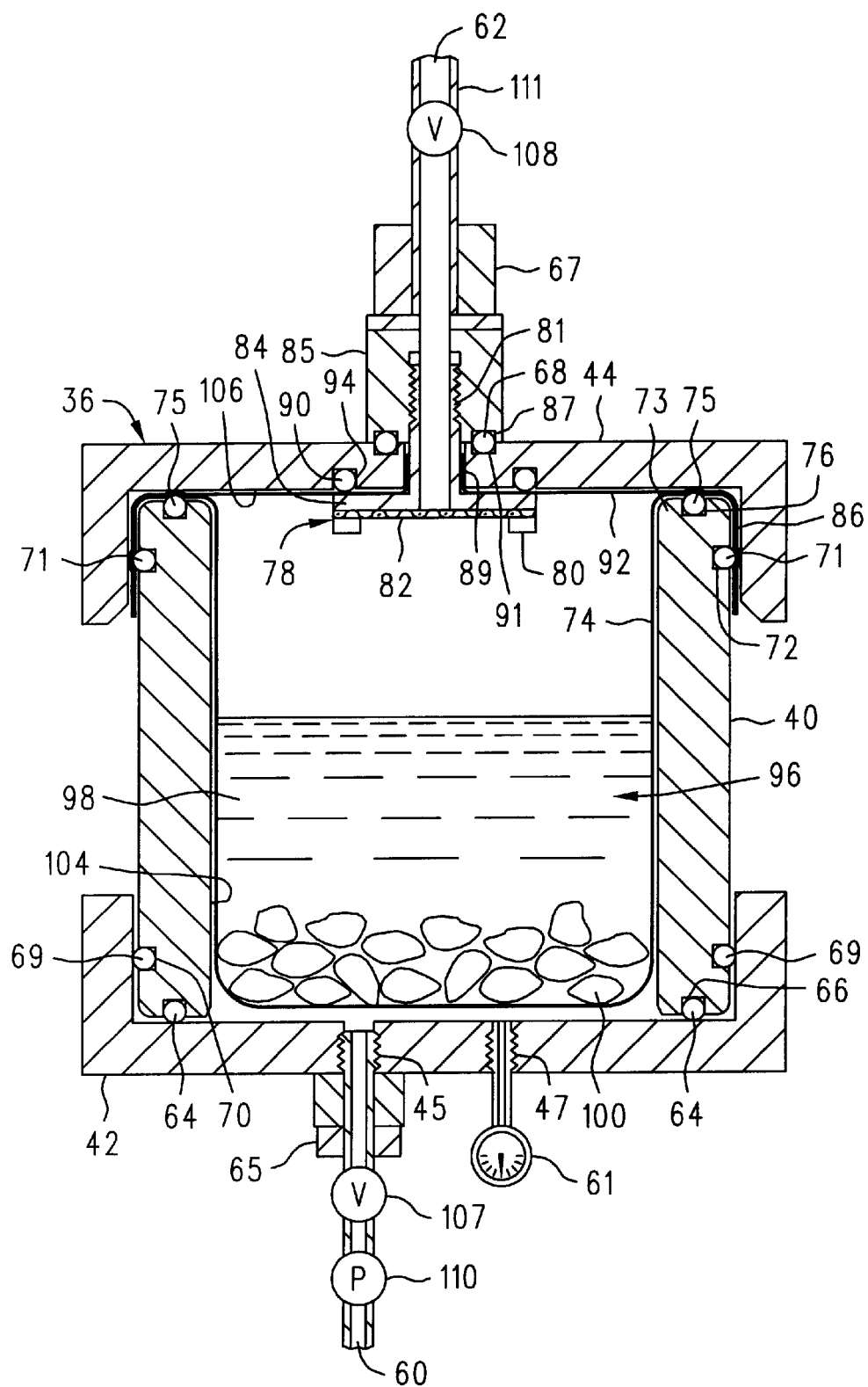
FIG. 6 is a schematic, cross-sectional view of a filtering apparatus produced in accordance with the invention showing the filter liners and solids before filtering.

As previously noted and with continued reference to FIGS. 2 and 3, inlet lid 42 has toggle clamps 46 mounted thereon which, when the apparatus 36 is assembled, are retained by catches 63 mounted on outlet lid 44. Pressure gauge 61 and inlet port 60 are secured to inlet lid 42 by threaded fittings 47 and 45, respectively, shown in detail in FIGS. 6 and 7. O-ring 64 fits in groove 66 of canister body 40 and O-ring 69 fits in groove 70, as best shown in FIG. 6. The O-rings 64 and 69 (which may be made from one or more materials conventionally used to produce O-ring structures including rubber and the like) serve to seal the canister body 40 and inlet lid 42 when toggle clamps 46 are engaged with catches 63. While the use of both O-rings 64 and 69 is preferred, and one of the two may be eliminated if desired. Mounting post 58, for attachment to rotating device 38, is secured to canister body 40 with bolts, not shown. With reference to FIGS. 3 and 6, O-ring 71 fits in groove 72 and O-ring 75 fits in groove 76 (not shown in FIG. 3) on outlet lip 73 of canister body 40.

Molded canister liner 74 (FIGS. 3, 4, and 6) is shaped to fit inside canister body 40 and overlap outlet lip 73 where it is sealed between O-rings 71, 75 and outlet lid liner 92 (FIGS. 3, 5, and 6) when the apparatus 36 is assembled and toggle clamps 46 are secured to catches 63. This sealing arrangement (namely, the sealable engagement of the canister liner 74 and lid liner 92 together) prevents any fluid from leaking into the surrounding regions of the canister body 40. O-rings 71, 75 (and all of the other O-rings set forth herein) are optimally made from the same materials discussed above in connection with O-rings 64, 6.

Figure 7:
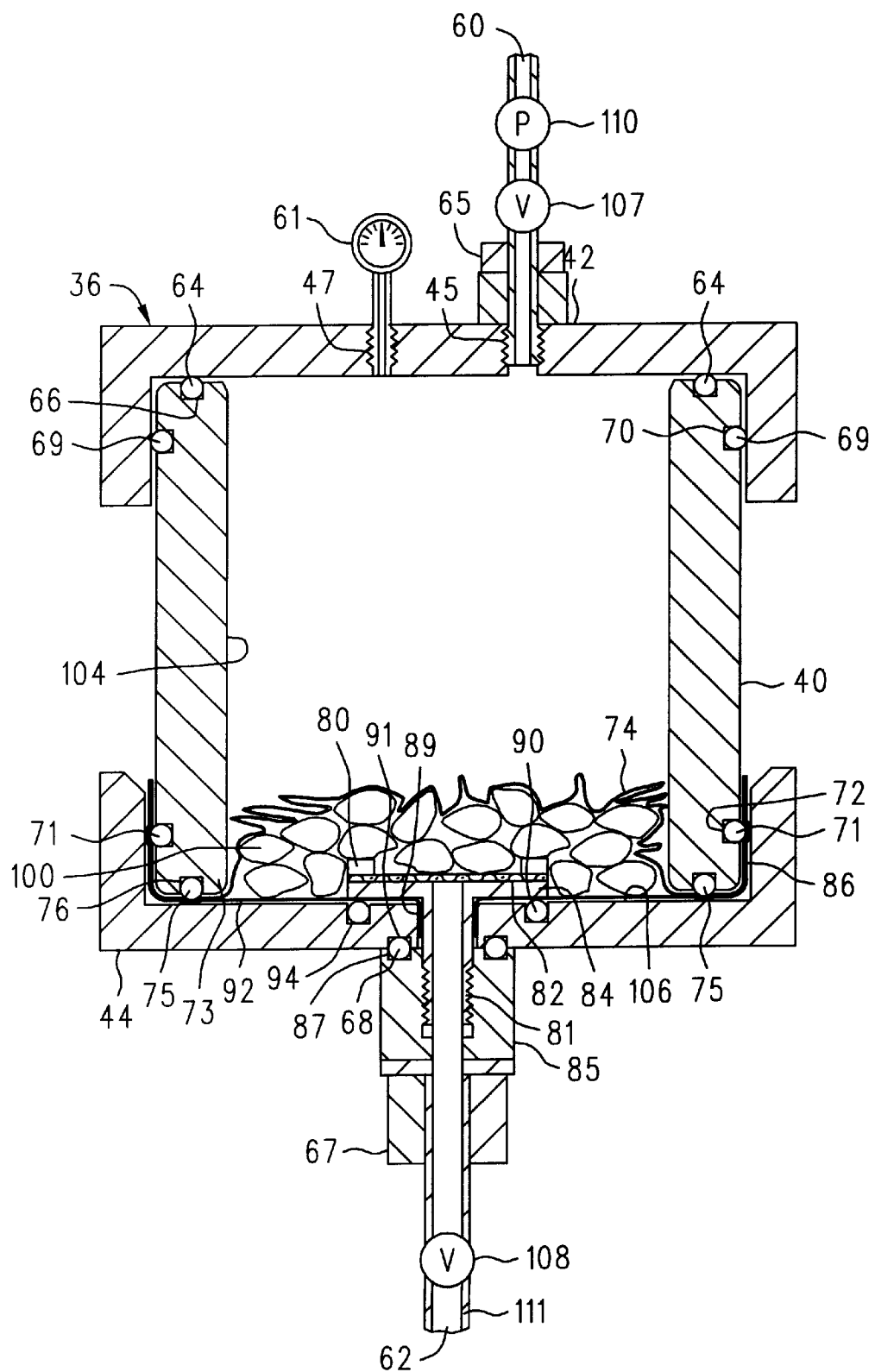
FIG. 7 is a schematic, cross-sectional view of the filtering apparatus of FIG. 6 showing the filter liners and solids after filtering with the apparatus being oriented in an inverted position.

Filter unit 78, as shown schematically in FIGS. 3, 6 and 7, comprises retaining ring 80, filter elements 82 with the desired size filtering holes or mesh, and filter base 84 with ridges 83. Ridges 83 prevent the filter elements 82 from sealing with filter base 84, thereby avoiding clogging. Base 84 includes a threaded coupling 81 best shown in FIGS. 6 and 7. Threaded coupling 81 slides through hole 88 in lid liner 92. O-ring 68 forms a seal between outlet lid 44 and adapter 85, with O-ring 68 being positioned in groove 87 in adapter 85 and within groove 91 in lid 44 as shown in FIG. 6. Screws 77 in holes 79 (FIG. 3) fasten retaining ring 80 and filter elements 82 to base 84. Filter elements 82 may be made of any suitable material with openings sized for a given application such as stainless steel, engineering plastic, aluminum, ceramic, glass, etc. Retaining ring 80 and base 84 may be made of any suitable metal or polymeric material with adequate physical properties including resistance to chemical attack by a sample. One skilled in the art would appreciate that the specific construction of the filter may involve many forms so long as it serves to separate the liquids from the solids in a sample.

A filter unit suitable for use in connection with the invention may be assembled from separate filter elements 82 comprising unit 78 as schematically shown in FIG. 3, or formed as a single unit. For example, an inexpensive filter element could be made by molding a polymeric holder around a metal screen mesh. Such a filter unit could be disposed of after a single use, if desired.

Molded lid liner 92 is shaped to fit inside outlet lid 44 and overlap lip 86 of canister liner 74. An opening or hole 88 within an upwardly-extending tubular section 89 (FIG. 5) is provided in liner 92 for the passage of fluids threrethrough. O-ring 90 fits in groove 94 in outlet lid 44. Liner 92 is held in place by filter unit 78 after filter base 84 is pushed through outlet lid 44 and screwed in place. Quick disconnect coupling 67 attaches to adapter 85. Adapter 85 screws onto threaded coupling 81 associated with filter base 84 causing O-ring 90 to form a seal around the outlet port 62. Likewise, O-rings 71, 75 serve on an individual and/or collective basis to sealaby engage the lid 44 and the lid liner 92 together. O-ring 90 also assists in this function.

Figure 4:
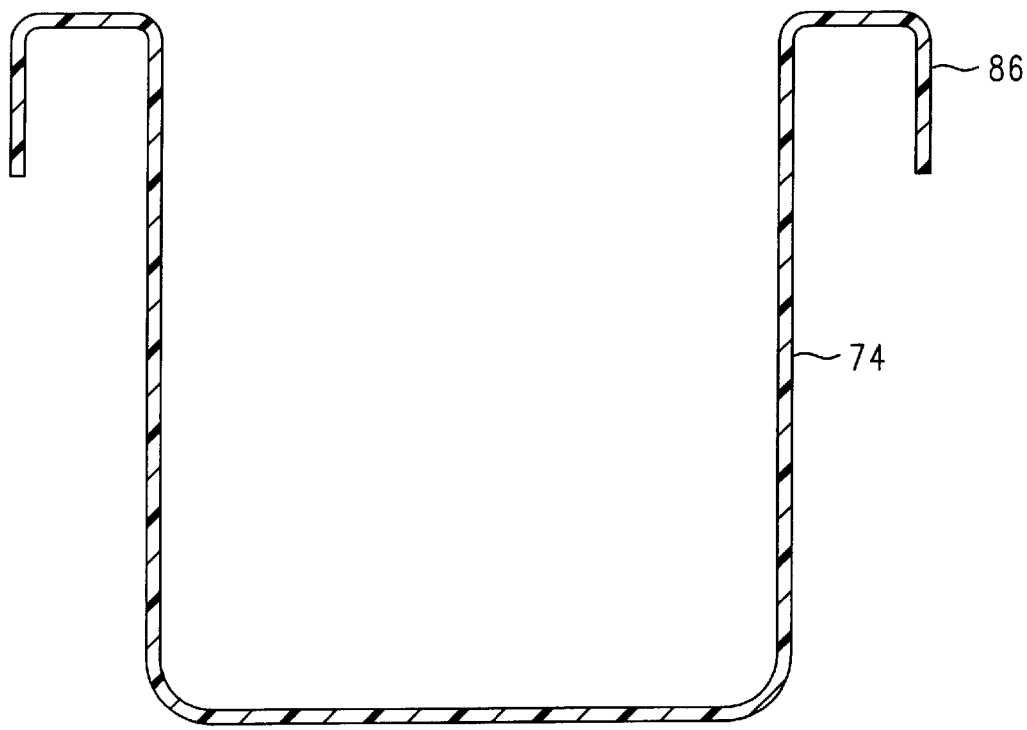
FIG. 4 is a schematic, cross-sectional view of a representative molded canister liner.
Figure 5:
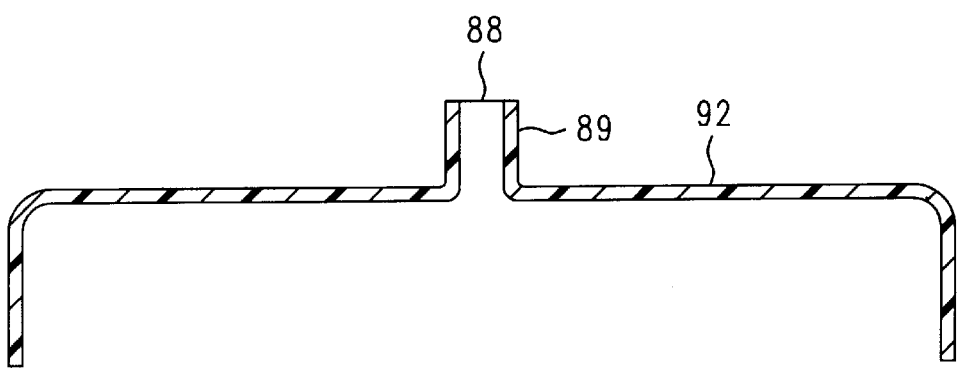
FIG. 5 is a schematic, cross-sectional view of a representative molded liner for the canister lid.

Canister liner 74 and lid liner 92 are shown in cross section in FIGS. 4 and 5, respectively. With further reference to FIG. 6, liners 74 and 92 are molded to fit the interior surfaces 104 and 106 of the canister body 40/inlet lid 42 combination and outlet lid 44, respectively. Liners 74 and 92, together, prevent contact between a sample 96, comprising solids 100 and fluid 98, and the interior surfaces 104, 106. The opening or hole 88 is again provided in lid liner 92 to allow the passage of fluid from sample 96 during the filtering process.

Liners 74 and 92 may be made of any suitable polymeric material (such as thermoplastic or thermosetting polymers) or rubber. Selection of a particular liner material is largely dependent on the type of sample to be filtered. An appropriate liner material must be impervious and/or resistant to damaging chemical attack by a sample, and the canister liner, at least, must be flexible at filtering temperatures. The polymeric material must also be tough enough to resist abrasion and puncture by sample solids 100.

Thermoplastic resins with suitable flexibility such as styrene, acrylics, cellulosics, polyethylene, polypropylene, vinyl chlorides, and polyamides may be used in connection with the liners 74, 92. Thermosetting resins such as ureas, natural rubbers and synthetic rubbers may also be employed. The liners 74, 92 can be manufactured by any suitable method such as compression molding, blow molding, vacuum molding, injection molding and so forth. Where extra strength is desired, the liners may be reinforced with fibrous, mat or woven materials, for example. Similarly, the canister body 40 and lids 42 and 44 may be made of any suitable metal, glass or polymeric material or a combination thereof.

In a preferred and non-limiting embodiment, liners 74, 92, each about 0.02 to 0.03 inches thick, are vacuum-molded from thermoplastic polytetrafluoroethylene sheet. This particular polymer is desirable because of its resistance to attack by almost any chemical as well as its mechanical toughness. These polytetrafluoroethylene liners were found to be particularly useful for performing filtrations under the SSW 846-TCLP procedure specified by the United States Environmental Protection Agency for conducting solvent extractions from soil samples. This procedure requires agitating the soil and liquid solvents for 16 hours and then performing the filtration. Samples in the current embodiment of the present invention are agitated by rotation of a filtering apparatus (such as apparatus 36) on a rotating device (such as device 38).

The several O-rings described above are present in the aforesaid embodiment to provide leak-proof operation of the filtering apparatus 36. While the O-rings may be made of any suitable elastomeric material as previously noted, viton rubber O-rings provide effective results and can be used repeatedly without damage.

Seals for the apparatus 36 have been shown and particularly discussed in terms of O-rings in grooves. However, the word "seal" and phrase "sealably engaged" as used herein shall be defined to involve the relationship of adjacent elements to prevent the is leakage of liquids between them. In the embodiments discussed above, when the O-rings are physically compressed, they form seals that do not allow the passage of liquids. Nonetheless, one skilled in the art will appreciate that how the seals are formed and leakage of liquid is prevented may be accomplished in a number of ways, be it by O-rings or other physical or mechanical arrangements so long as liquid leakage is prevented. For example, the canister and lid liners 74, 92 could be formed of rubber sheet material that would create liquid-tight seals when the lid 44 is positioned on canister body 40. Alternatively, a liquid-resistant bead of a compressible grease, putty, or adhesive material could be used to form the seals. Many other such arrangements would be apparent to one skilled in the art.

Referring again to FIG. 6, sample 96 is filtered in apparatus 36 as follows. O-rings 64, 69, 71 and 75 are positioned in the appropriate grooves of canister body 40. Canister body 40 is set in inlet lid 42. Molded canister liner 74 is placed into canister body 40. Sample 96 comprising fluid 98 and solids 100 is put into liner 74. O-ring 90 is positioned in groove 94 of outlet lid 44. Lid liner 92 is set in outlet lid 44 adjacent interior surface 106. Filter unit 78 is positioned in lid 44 and held in place by threadable engagement of the female coupling adapter 85 with the male coupling 81 of filter base 84, thereby forming a seal with O-ring 90 in groove 94 so that the filter unit 78 and lid liner 92 are sealably engaged together. Outlet lid 44 is positioned over canister body 40 and toggle clamps 46 (see FIGS. 2 and 3) are secured to catches 63. The several O-rings form liquid-tight seals between lid liner 92 and canister liner 74, and between lid liner 92 and outlet lid 44 around outlet port 62. This seal arrangement is clearly illustrated in FIG. 6.

In a representative embodiment, depicted in FIG. 7, apparatus 36 is simply inverted after it is assembled so that the outlet port 62 is located below the inlet port 60. A first or "inlet" valve 107, in line with (e.g. operatively connected to) inlet port 60, is opened to let air in and prevent the creation of a vacuum in canister body 40. A second or "outlet" valve 108, in line with (e.g. operatively connected to) outlet port 62, is opened to allow the passage of fluid 98 through filter elements 82 of unit 78, into line 111 associated with outlet port 62, and into a sample container (not shown). The weight of sample 96 encourages lid liner 92 to form a seal with outlet lid 44 at O-ring 90. Solids 100 are trapped inside collapsed canister liner 74.

In another embodiment, a pressurized fluid 110 such as air or water is delivered into canister body 40 through valve 107 to assist and accelerate the filtration process. Gauge 61 measures the pressure of fluid 110 in canister body 40, with said pressure assisting the collapse of liner 74 and the flow of fluid 98 through outlet port 62. Similarly, a vacuum may be drawn through outlet port 62 in lid 44 while valve 107 (and preferably valve 108) are opened to facilitate the filtration process. The procedures discussed above create a pressure differential in canister body 40 and optimally the collapse of liner 74 which causes fluid 98 to be forced through the filter elements 82 and outlet port 62 in lid 44.

A source (not shown) for heating or cooling a sample 96 in the canister body 40 may also be provided to control the temperature during the filtration process.

It is apparent that only liners 74 and 92, outlet port 62, filter unit 78, and any plumbing downstream thereof are contaminated by sample 96. Solids 100 remain in the package formed by lid liner 92 and canister liner 74. The liners 74, 92 and filter unit 78 may be disposed of or cleaned and reused as desired. Outlet port 62 and downstream plumbing are easily flushed and cleaned. Any vacuum built up in the liners 74 and 92, or the interior of canister body 40, during filtering can be readily relieved by opening inlet valve 107, outlet valve 108, or both, to atmosphere.

After filtration, apparatus 36 is easily disassembled. Liners 74 and 92, filter unit 78, and solid material 100 can be removed together without contaminating interior surfaces 104 and 106. Little or no cleaning of apparatus 36 is required before filtering another sample, so the rate at which samples can be processed is much improved over the prior art. The equipment is so easily taken apart that no damage is done to the O-rings or other seals which may be used. Because the sample constituents are contained by the liners, and because they never come in contact with a human operator, the subject invention is useful for filtering hazardous or potentially hazardous materials. Moreover, the apparatus 36 is easy enough to assemble and disassemble that these activities may be done by robots or other remotely controlled means.

EXAMPLE

A soil sample consisting of small gravel, sharp rocks, sticks, metal shavings and sandy dirt was mixed with water. The sample was placed in an apparatus like that described above. The canister and lid liners were formed of compression molded polytetrafluoroethylene sheet material about 0.02 to 0.03 inches thick. The canister was made of polycarbonate and the lids were made of machined aluminum.

The filter unit comprised a stainless steel retaining ring and a stainless steel base. The filter assembly comprised two stainless steel mesh screens sandwiching a microporous filter. One such microporous filter is the Millipore AP, catalog item number AP40 142 50 prefilter. The relatively fragile microporous filter is protected from tearing and abrasion by the more rugged stainless steel mesh screens. The screens and filter were secured between the retaining ring and the base.

The open-ended canister was placed on the inlet lid and the molded canister liner was set in place. The sample was placed in the canister liner. The lid liner was positioned in the outlet lid and the filter element base was screwed into the outlet lid forming a seal around the outlet among and between the filter element, lid liner and the outlet lid. The canister and lids were clamped shut and mounted on a rotating device. The valves to the inlet and outlet ports were closed. The sample was rotated in the clamped canister for about 16 hours at room temperature.

The canister was then fixed in position so that the outlet port was on the bottom and the inlet port was on the top as per FIG. 7. A container for the fluid was positioned under the outlet port. The inlet and outlet valves were opened and the fluid was filtered from the container following the United States Environmental Protection Agency's SSW 846-TCLP method.

The apparatus was disassembled, the solids were disposed of, and the liners and filter components were cleaned preparatory to reuse. The outlet port and downstream plumbing were flushed with water, completely cleaning the apparatus and preparing it for reuse.

In summary, we have invented a filter system or filtering apparatus that comprises an open canister having an inlet port therein. A canister lid (also characterized herein as an "outlet lid") is provided for the open canister, which lid has an outlet port for the passage of fluids from the canister. Liners are provided for the canister and lid, respectively. These liners are shaped to fit the interior of the canister and the inner surface of the lid. The canister liner is optimally flexible at filtering temperatures so that it can collapse around the trapped solids. The lid liner may or may not be flexible, so long as liquid-tight seals are formed. The sample to be filtered is positioned in the canister liner prior to placing the canister lid on the open canister.

When the apparatus is assembled for filtering, a filter, preferably in a filter element assembly, is located adjacent the lid liner. When the lid is placed on the canister and clamped or otherwise held in place, the lid liner and the canister liner are sealed together. A hole is provided in the lid liner to allow the exit of liquid (e.g. fluid) from the canister through the outlet port in the canister lid.

The sample is preferably filtered by creating a pressure differential between the interior of the canister and the canister liner. As a result, the canister liner collapses around the solids and forces liquid from the sample through the outlet port. This may be accomplished by inverting the filtering apparatus and opening the inlet port to atmosphere.

The canister and lid liners are formed of a material that is chemically impervious to the sample and tough enough to withstand abrasion from must solids without puncturing or tearing. The canister liner should also be flexible under filtering conditions. Because of the liners, the interior surfaces of the canister and lid are not contaminated by the sample.

The system is easily disassembled by removing the lid from the canister and then removing the filter element assembly and liners. In a preferred practice, the seal between the lid liner and canister liner remains in place due to the vacuum formed when the fluid is removed. As a result, the lid liner, canister liner, filtered solids, and filtration components can be removed as a single assembly. The assembly may then be dismantled and disposed of as is. If the retained solids are of interest for further examination, they may be stored in the collapsed canister liner-lid liner package. A stopper of some sort known to those skilled in the art can be used to plug the outlet hole in the lid liner. In another practice, the entire package, or just the filtered solids, could be stored in air-tight shrink wrap or an evacuated, sealed bag well known in the art.

To clean the apparatus and prepare it for another sample, the system elements downstream of the outlet for fluid removal are flushed. New canister and lid liners and a clean filter are provided, and the apparatus is ready to filter another, different kind of sample without danger of cross contamination. The cleaning process may be done by an operator or automatically by a robot or other such manipulation device.

Our invention provides an efficient method and apparatus that are particularly well-adapted for work in the environmental clean-up of contaminated soil. The apparatus is easy to use and clean. It is also resistant to damage during use or cleaning. Employing the specially adapted canister and lid liners prevents contamination of humans with potentially hazardous materials. The liners also prevent contamination of the interior surfaces of the equipment. The apparatus is easy enough to operate that it may be remotely manipulated by a robot or other such mechanical manipulator as previously stated, a feature particularly useful when dealing with radioactive or poisonous materials.

While our invention has been described in terms of specific embodiments thereof, other forms may be readily adapted by one skilled in the art that remain within the scope of the invention. For example, one skilled in the art could choose different materials to fabricate the apparatus. Different sealing configurations could provide liquid and air-tight seals. Different clamping arrangements could be made. The tubing used for the outlet could be disposable. The canister could be made in a single piece with a hinged lid, and so forth. Accordingly, the scope of this invention shall be defined in accordance with the following claims.

We claim:

1. A filter apparatus for separating solids from liquids in a sample, the filter apparatus comprising:
   a canister;
   a canister liner for use in lining the canister, the canister liner being substantially chemically impervious to the sample;
   a lid for the canister, the lid comprising an outlet port therein for removing liquids filtered from the sample;
   a lid liner for use in lining the lid, the lid liner being substantially chemically impervious to the sample and comprising an opening therein for passage of liquids filtered from the sample, said lid liner being sealably engaged to the canister liner and also being sealably engaged to the lid; and
   at least one filter element located adjacent the lid liner.

2. The apparatus of claim 1 wherein the filter element is reusable.

3. The apparatus of claim 1 wherein the filter element is disposable.

4. The apparatus of claim 1 wherein the canister liner is comprised of a material selected from the group consisting of a thermoplastic polymer, a thermosetting polymer, and rubber.

5. The apparatus of claim 1 wherein the canister liner is comprised of polytetrafluoroethylene.

6. The apparatus of claim 1 wherein the canister liner is flexible.

7. A filter apparatus for separating solids from liquids in a sample, the filter apparatus comprising:
   a canister comprising an inlet port therein;
   a flexible canister liner for use in lining the canister, the canister liner being substantially chemically impervious to the sample;
   a lid for the canister, the lid comprising an outlet port therein for removing liquids filtered from the sample;

a lid liner for use in lining the lid, the lid liner being substantially chemically impervious to the sample and comprising an opening therein for passage of liquids filtered from the sample, said lid liner being sealably engaged to both the canister liner and the lid;

a filter unit located adjacent the lid liner, the filter unit comprising at least one filter element, said lid liner also being sealably engaged to the filter unit;

a first valve operatively connected to the inlet port; and a second valve operatively connected to the outlet port.

8. The apparatus of claim 7 wherein the filter element is reusable.

9. The apparatus of claim 7 wherein the filter element is disposable.

10. The apparatus of claim 7 wherein the filter unit further comprises a retaining ring and a base member comprising a plurality of ridges thereon, the filter element being positioned between the retaining ring and the base member.

11. The apparatus of claim 7 further comprising a source of pressurized fluid in fluid communication with the inlet port.

12. The apparatus of claim 7 wherein the canister liner is comprised of a material selected from the group consisting of a thermoplastic polymer, a thermosetting polymer, and rubber.

13. The apparatus of claim 7 wherein the canister liner is comprised of polytetrafluoroethylene.

14. A method for separating solids from liquids in a sample comprising:

providing a canister;

placing a canister liner in the canister;

placing the sample in the canister liner within the canister;

providing a lid sealable with the canister, the lid comprising an outlet port therein for passage of liquids;

providing a lid liner for use in lining the lid, the lid liner comprising an opening therein for passage of liquids;

providing a filter element located adjacent the lid liner;

forming a liquid-tight seal between the canister liner and the lid liner;

forming a liquid-tight seal between the lid and the lid liner; and causing the liquids in the sample to be forced through the filter element and the outlet port in the lid, with the solids being retained in the canister liner.

15. The method of claim 14 wherein said causing of the liquids to be forced through the filter element and the outlet port in the lid comprises collapsing the canister liner within the canister so that the liquids are forced therefrom.

16. A method for separating solids from liquids in a sample comprising:

providing a canister, the canister comprising an inlet port therein;

placing a canister liner in the canister;

placing the sample in the canister liner within the canister;

providing a lid sealable with the canister, the lid comprising an outlet port therein for passage of liquids;

providing a lid liner for use in lining the lid, the lid liner comprising an opening therein for passage of liquids;

providing a filter unit located adjacent the lid liner, the filter unit comprising at least one filter element;

forming a liquid-tight seal between the canister liner and the lid liner;

forming a liquid-tight seal between the lid and the lid liner;

forming a liquid-tight seal between the lid liner and the filter unit; and creating a pressure differential in the canister such that the liquids are forced through the filter element and the outlet port in the lid, with the solids being retained in the canister liner.

17. The method of claim 16 wherein the creating of the pressure differential comprises introducing a pressurized gas into the canister through the inlet port.

18. The method of claim 16 wherein the creating of the pressure differential comprises orienting the canister such that the outlet port is located below the inlet port.

19. The method of claim 16 wherein the creating of the pressure differential comprises drawing a vacuum through the outlet port in the lid.

* * * * *